(12) United States Patent
Würtz et al.

(10) Patent No.: US 6,743,754 B2
(45) Date of Patent: Jun. 1, 2004

(54) HERBICIDAL COMPOSITIONS

(75) Inventors: Jochen Würtz, Bingen am Rhein (DE); Jean Kocur, Hofheim (DE); Hans-Peter Krause, Hofheim (DE); Julio Martinez de Una, Liederbach (DE); Detlev Haase, Frankfurt (DE); Udo Bickers, Wietmarschen (DE); Gerhard Schnabel, Elsenfeld (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/882,441

(22) Filed: Jun. 15, 2001

(65) Prior Publication Data

US 2002/0091066 A1 Jul. 11, 2002

(30) Foreign Application Priority Data

Jun. 19, 2000 (DE) .......................... 100 29 169

(51) Int. Cl.⁷ .................. A01N 25/30; A01N 47/36
(52) U.S. Cl. .................. 504/212; 504/213; 504/214; 504/215; 504/358
(58) Field of Search .................. 504/212, 213, 504/214, 215, 358

(56) References Cited

U.S. PATENT DOCUMENTS

| 5,731,264 A | 3/1998 | Narayanan et al. ......... 504/116 |
| 6,313,074 B1 | * 11/2001 | Suzuki et al. ............... 504/362 |
| 6,479,432 B1 | * 11/2002 | Sixl ........................... 504/103 |

FOREIGN PATENT DOCUMENTS

| CA | 2093377 | 10/1994 |
| DE | 44 40 354 A1 | 5/1996 |
| EP | 0 007 687 | 2/1980 |
| EP | 0 030 138 | 6/1981 |
| EP | 0 681 865 | * 4/1995 |
| EP | 0 968 649 | 1/2000 |
| WO | WO 98/42192 | 10/1998 |

OTHER PUBLICATIONS

Jerry M. Green, "Optimizing Alcohol Ethoxylate Surfacant Activity at Low Doses", Weed Technology, 1999, vol. 13, pp. 737–740.
Green et al, "Surfacant Structure and Concentration Strongly Affect Rimsulfuron Activity", Weed Technology, 1993, vol. 7, pp. 633–640, also referred to as XP 000882663.

* cited by examiner

*Primary Examiner*—S. Mark Clardy
(74) *Attorney, Agent, or Firm*—Frommer Lawrence & Haug LLP

(57) ABSTRACT

The present invention relates to a herbicidal composition comprising

A) one or more sulfonylureas of the formula (I) and/or their salts

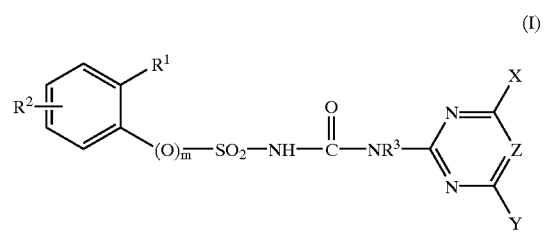

in which $R^1$ is $C_2$–$C_4$-alkoxy or CO—$R^a$, where $R^a$ is OH, $C_1$–$C_6$-alkoxy or $NR^bR^c$, where $R^b$ and $R^c$ independently of one another are identical or different and are H or $C_1$–$C_6$-alkyl, $R^2$ is halogen or $(A)_n$—$NR^dR^e$, where n is zero or 1, A is a group $CR^fR^g$, where $R^f$ and $R^g$ independently of one another are identical or different and are H or $C_1$–$C_6$-alkyl, $R^d$ is H or $C_1$–$C_6$-alkyl and $R^e$ is H, $C_1$–$C_6$-alkyl or an acyl radical, where $R^d$ and $R^e$ may also form a heterocyclic ring and where, if $R^1$ is $C_2$–$C_4$-alkoxy, $R^2$ may also be H, $R^3$ is H or $C_1$–$C_6$-alkyl, m is zero or 1, X and Y independently of one another are identical or different and are $C_1$–$C_6$-alkyl, $C_1$–$C_6$-alkoxy or $C_1$–$C_6$-alkylthio, where each of the three radicals mentioned is unsubstituted or substituted by one or more radicals selected from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$-$C_6$-alkynyloxy, preferably $C_1$–$C_4$-alkyl or $C_1$–$C_4$-alkoxy, Z is CH or N, and B) one or more surfactants comprising as structural element at least 10 alkylene oxide units.

14 Claims, No Drawings

HERBICIDAL COMPOSITIONS

The invention lies in the technical field of the crop protection products; in particular, the invention relates to herbicidal compositions comprising certain sulfonylureas and/or their salts and specific surfactants, which compositions are outstandingly suitable for controlling harmful plants in crop plants.

The use of sulfonylureas as active component of crop protection compositions is known (for example EP-A-007 687, EP-A-030 138). Likewise, it is known to combine sulfonylureas such as nicosulfuron (Accent®) with surfactants (for example Weed Technology 1999, Vol. 13, pages 737–740).

It was an object of the present invention to provide herbicidal compositions having particularly high herbicidal activity.

Surprisingly, it has now been found that this object is achieved by herbicidal compositions which comprise certain sulfonylureas in combination with specific surfactants.

The present invention thus relates to herbicidal compositions comprising

A) one or more sulfonylureas of the formula (I) and/or their salts

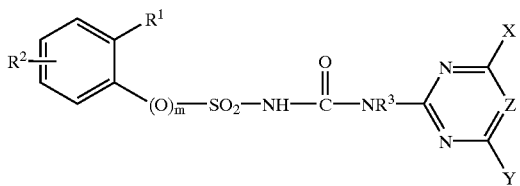

(I)

in which
R$^1$ is C$_2$–C$_4$-alkoxy or CO—R$^a$, where R$^a$ is OH, C$_1$–C$_6$-alkoxy or NR$^b$R$^c$, where R$^b$ and R$^c$ independently of one another are identical or different and are H or C$_1$–C$_6$-alkyl,
R$^2$ is halogen or (A)$_n$—NR$^d$R$^e$, where n is zero or 1, A is a group CR$^f$R$^g$, where R$^f$ and R$^g$ independently of one another are identical or different and are H or C$_1$–C$_6$-alkyl, R$^d$ is H or C$_1$–C$_6$-alkyl and R$^e$ is H, C$_1$–C$_6$-alkyl or an acyl radical, where R$^d$ and R$^e$ may also form a heterocyclic ring and where, if R$^1$ is C$_2$–C$_4$-alkoxy, R$^2$ may also be H,
R$^3$ is H or C$_1$–C$_6$-alkyl,
m is zero or 1,
X and Y independently of one another are identical or different and are C$_1$–C$_6$-alkyl, C$_1$–C$_6$-alkoxy or C$_1$–C$_6$-alkylthio, where each of the three radicals mentioned is unsubstituted or substituted by one or more radicals selected from the group consisting of halogen, C$_1$–C$_4$-alkoxy and C$_1$–C$_4$-alkylthio, or are C$_3$–C$_6$-cycloalkyl, C$_2$–C$_6$-alkenyl, C$_2$–C$_6$-alkynyl, C$_3$–C$_6$-alkenyloxy or C$_3$–C$_6$-alkynyloxy, preferably C$_1$–C$_4$-alkyl or C$_1$–C$_4$-alkoxy,
Z is CH or N, and
B) one or more surfactants comprising as structural element at least 10, preferably 10–200, alkylene oxide units.

Surfactant B) preferably contains 10–150 alkylene oxide units, one or more C$_1$–C$_{40}$-carbon-containing radicals and optionally one or more polar functional groups.

The term alkylene oxide units is preferably to be understood as meaning units of C$_2$–C$_{10}$-alkylene oxides, such as ethylene oxide, propylene oxide, butylene oxide or hexylene oxide, where the units within the surfactant may be identical to or different from one another.

Suitable polar functional groups are, for example, anionic groups, such as carboxylate, carbonate, sulfate, sulfonate, phosphate or phosphonate, cationic groups, such as groups having a cationic nitrogen atom, for example a pyridinium group or an —NR$^y_3$ group, where R$^y$ are identical or different and are H or unsubstituted or substituted C$_1$–C$_{10}$-hydrocarbon radicals, such as C$_1$–C$_{10}$-alkyl, electrically neutral polar groups, such as carbonyl, imine, cyano or sulfonyl, or betainic groups, such as

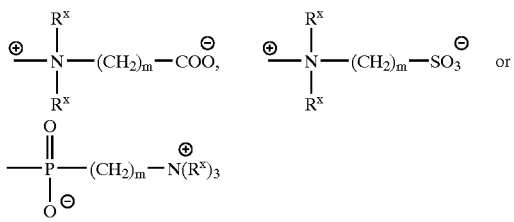

where m=1, 2, 3, 4 or 5 and R$^x$ are identical or different unsubstituted or substituted C$_1$–C$_{10}$-hydrocarbon radicals, such as C$_1$–C$_{10}$-alkyl.

Preferably, the composition according to the invention comprises, as component B), one or more surfactants of the formula (II)

(II)

in which
EO is an ethylene oxide unit,
PO is a propylene oxide unit,
x is an integer from 1 to 50,
y is an integer from 0 to 50,
z is an integer from 0 to 50,
where the sum (x+y+z) is ≧10 and ≦150, and
R$^4$ is OH, an unsubstituted or substituted C$_1$–C$_{40}$-hydrocarbonoxy radical, an O-acyl radical, such as O—COR$^I$, O—CO—OR$^I$, O—CO—NR$^I$R$^{II}$, O—P(O)(R$^I$)[(EO)$_u$(OR$^{II}$)] or O—P(O)[(EO)$_u$(OR$^I$)][(EO)$_v$(OR$^{II}$)], or NR$^I$R$^{II}$ or [NR$^I$R$^{II}$R$^{III}$]$^⊕$X$^⊖$, where R$^I$, R$^{II}$ and R$^{III}$ are identical or different and are H or an unsubstituted or substituted C$_1$–C$_{30}$-hydrocarbon radical which may be attached via a group (EO)$_w$, where w is an integer from 1 to 50, X$^⊖$ being an anion (for example the anion of an organic acid, such as a carboxylic acid anion, for example acetate or lactate, or the anion of an inorganic acid, such as ½ sulfate, [O—SO$_3$—CH$_3$]$^⊖$, sulfonate, ⅓ phosphate, phosphonate or halide, such as Cl$^⊖$ or Br$^⊖$), and u and v independently of one another being integers from 0 to 50, and
R$^5$ is H, an unsubstituted or substituted C$_1$–C$_{40}$-hydrocarbon radical, an acyl radical, such as COR$^I$, CO—OR$^I$, CO—NR$^I$R$^{II}$, P(O)(R$^I$)[(EO)$_u$(OR$^{II}$)] or P(O)[(EO)$_u$(OR$^I$)][(EO)$_v$(OR$^{II}$)], or NR$^I$R$^{II}$ or [NR$^I$R$^{II}$R$^{III}$]$^⊕$X$^⊖$, where R$^I$, R$^{II}$ and R$^{III}$ are identical or different and are H or an unsubstituted or substituted C$_1$–C$_{30}$-hydrocarbon radical which may be attached via a group (EO)$_w$, where w is an integer from 1 to 50, X$^⊖$ being an anion (for example the anion of an organic acid, such as a carboxylic acid anion, for example acetate or lactate, or the anion of an inorganic acid, such as ½ sulfate, [O—SO$_3$—CH$_3$]$^⊖$, sulfonate, ⅓ phosphate, phosphonate or halide, such as Cl⁻ or Br⁻), and u and v independently of one another being integers from 0 to 50.

The abbreviation EO in formula (II) denotes an ethylene oxide unit, likewise when used in the definition of $R^4$ and $R^5$.

Preference is given to surfactants of the formula (II) in which the sum (x+y+z) is $\geq 10$ and $\leq 150$, preferably 11–100, particularly preferably 12–80, and $R^4$ is OH, an unsubstituted or substituted $C_1$–$C_{30}$-, preferably $C_4$–$C_{20}$-, hydrocarbonoxy radical, such as a $C_8$-, $C_{10}$-, $C_{12}$-, $C_{13}$- (for example isotridecyl-), $C_{14}$-, $C_{16}$-, $C_{18}$-, $C_{20}$-alkoxy radical, -alkenyloxy radical or -alkynyloxy radical, or an unsubstituted or substituted, for example mono- or poly-$C_1$–$C_{20}$-alkyl-substituted, $C_6$–$C_{14}$-aryloxy radical, such as p-octylphenoxy, p-nonylphenoxy, 2,4-dibutylphenoxy, 2,4,6-triisobutylphenoxy, 2,4,6-tri-n-butylphenoxy or 2,4,6-tri-sec-butylphenoxy, or $R^4$ is O—CO—R$^I$, O—COOR$^I$, NR$^I$R$^{II}$ or [NR$^I$R$^{II}$R$^{III}$]$^\oplus$X$^\ominus$, where R$^I$, R$^{II}$ and R$^{III}$ are identical or different and are H, an unsubstituted or substituted $C_8$–$C_{30}$-, preferably $C_4$–$C_{20}$-, hydrocarbon radical, such as a $C_8$-, $C_{10}$-, $C_{12}$-, $C_3$- (for example isotridecyl-), $C_{14}$-, $C_{16}$-, $C_{18}$-, $C_{20}$-alkyl radical, -alkenyl radical or -alkynyl radical, or an unsubstituted or substituted, for example mono- or poly-$C_1$–$C_{20}$-alkyl-substituted, $C_6$–$C_{14}$-aryl radical, such as p-octylphenyl, p-nonylphenyl, 2,4-dibutylphenyl, 2,4,6-triisobutylphenyl, 2,4,6-tri-n-butylphenyl or 2,4,6-tri-sec-butylphenyl, or R$^I$, R$^{II}$ and R$^{III}$ are identical or different (EO)$_w$-R$^{IV}$, where R$^{IV}$ is H or an unsubstituted or substituted $C_1$–$C_{20}$-hydrocarbon radical, such as a $C_8$-, $C_{10}$-, $C12$,$C_{13}$- (for example isotridecyl-), $C_{14}$-, $C_{16}$-, $C18$-, $C_{20}$-alkyl radical, -alkenyl radical or -alkynyl radical, or an unsubstituted or substituted, for example mono- or poly-$C_1$–$C_{20}$-alkyl-substituted, $C_6$–$C_{14}$-aryl radical, such as p-octylphenyl, p-nonylphenyl, 2,4-dibutylphenyl, 2,4, 6-triisobutylphenyl, 2,4,6-tri-n-butylphenyl or 2,4,6-tri-sec-butylphenyl, and w is an integer from 1 to 50, X$^\ominus$ being an anion, and $R^5$ is H, an unsubstituted or substituted $C_1$–$C_{30}$-, preferably $C_1$–$C_{20}$-, hydrocarbon radical, such as a $C_1$-, $C_2$-, $C_3$-, $C_4$-, $C_5$-, $C_6$-, $C8$-, $C_{10}$-, $C_{12}$-, $C_{13}$- (for example isotridecyl-), $C_{14}$-, $C_{16}$-, $C_{18}$, $C_{20}$-alkyl radical, -alkenyl radical or -alkynyl radical, or an unsubstituted or substituted, for example mono- or poly-$C_1$–$C_{20}$-alkyl-substituted, $C_6$–$C_{14}$-aryl radical, such as p-octylphenyl, p-nonylphenyl, 2,4-dibutylphenyl, 2,4, 6-triisobutylphenyl, 2,4,6-tri-n-butylphenyl or 2,4,6-tri-sec-butylphenyl, or $R^5$ is CO—R$^I$, COOR$^I$, NR$^I$R$^{II}$ or [NR$^I$R$^{II}$R$^{III}$]$^\oplus$X$^\ominus$, where R$^I$, R$^{II}$ and R$^{III}$ are identical or different and are H, an unsubstituted or substituted $C_1$–$C_{30}$-, preferably $C_1$–$C_{20}$-, hydrocarbon radical, such as a $C_1$-, $C_2$-, $C_3$-, $C_4$-, $C_5$-, $C_6$-, $C_8$- $C_{10}$, $C_{12}$, $C_{13}$- (for example isotridecyl-), $C_{,14}$-, $C_{16}$-, $C_{18}$-, $C_{20}$-alkyl radical, -alkenyl radical or -alkynyl radical, or an unsubstituted or substituted, for example mono- or poly-$C_1$–$C_{20}$-alkyl-substituted, $C_6$–$C_{14}$-aryl radical, such as p-octylphenyl, p-nonylphenyl, 2,4-dibutylphenyl, 2,4,6-triisobutylphenyl, 2,4,6-tri-n-butylphenyl or 2,4,6-tri-sec-butylphenyl, or R$^I$, R$^{II}$ and R$^{III}$ are identical or different (EO)$_w$-R$^{IV}$, where R$^{IV}$ is H or an unsubstituted or substituted $C_1$–$C_{30}$-, preferably $C_1$–$C_{20}$-, hydrocarbon radical, such as a $C_1$-, $C_2$-, $C_3$-, $C_4$-, $C_5$- $C_6$-, $C_8$-, $C_{10}$-, $C_{12}$-, $C_{13}$- (for example isotridecyl-), $C_{14}$-, $C_{16}$-, $C_{18}$-, $C_{20}$-alkyl radical, -alkenyl radical or -alkynyl radical, or an unsubstituted or substituted, for example mono- or poly-$C_1$–$C_{20}$-alkyl-substituted, $C_6$–$C_{14}$-aryl radical, such as p-octylphenyl, p-nonylphenyl, 2,4-dibutylphenyl, 2,4, 6-triisobutylphenyl, 2,4,6-tri-n-butylphenyl or 2,4,6-tri-sec-butylphenyl, and w is an integer from 1 to 50, X$^\ominus$ being an anion.

Particular preference is given to surfactants of the formula (II) in which the sum (x+y+z) is 11–80, preferably 12–50, $R^4$ is ($C_8$–$C_{18}$)-alkoxy, ($C_8$–$C_{18}$)-alkenyloxy or ($C_8$–$C_{18}$)-alkynyloxy, ($C_7$–$C_{17}$)-alkylcarbonyloxy, ($C7$–$C_{17}$)-alkenylcarbonyloxy, ($C_7$–$C_{17}$)-alkynylcarbonyloxy or ($C_1$–$C_{10}$)-alkylphenoxy, such as octylphenoxy, p-nonylphenoxy, 2,4,6-tri-n-butylphenoxy, 2,4,6-triisobutylphenoxy or 2,4,6-tric-sec-butylphenoxy, and $R^5$ is H, ($C_1$–$C_8$)-, preferably ($C_1$–$C_6$)-, alkyl, ($C_2$–$C_{18}$)-, preferably ($C_2$–$C_6$)-, alkenyl or ($C_2$–$C_{18}$)-, preferably ($C_2$–$C_6$)-, alkynyl, CO—H, CO—($C_1$–$C_{17}$)-alkyl, CO—($C_2$–$C_{17}$)-alkenyl or CO-($C_2$–$C_{17}$)-alkynyl.

Sufactants B), for example of the formula (II), are known from the literature, for example from McCutcheon's Emulsifiers & Detergents 1994, Vol. 1: North American Edition and Vol. 2, International Edition; McCutcheon Division, Glen Rock N.J., USA and from "Surfactants in Consumer Products", J. Falbe, Springer-Verlag Berlin, 1987. The Surfactants B) mentioned in these publications are expressly incorporated Herein by way of reference. Moreover, surfactants B), for example of the formula (II), are also commercially available, for example under the trade names Genapol® X- or O- or T-series, Sapogenat® T-series, Arkopol® N-series, Afilan® PTU, Hordaphos® and Emulsogen®-series from Clariant AG; Agrilan®-types from Akcros Organics; Alkamul® and Antarox®-types from Rhodia; Emulan®-types (NP, OC, OG, OK) from BASF AG; Dehydol®-types from Henkel; Agent W®-types from Stepan Company; Crodamel®-types from Croda GmbH. The surfactants B) mentioned in the respective product leaflets are expressly incorporated herein by way of reference.

Examples of surfactants B), for example of the formula (II), are listed in table 1 below:

TABLE 1

| Ex. No. | $R^4$ | x | y | z | $R^5$ |
|---|---|---|---|---|---|
| 1 | octyl-O— | 10 | — | — | H |
| 2 | " | 12 | — | — | H |
| 3 | " | 15 | — | — | H |
| 4 | decyl-O— | 10 | — | — | H |
| 5 | " | 15 | — | — | H |
| 6 | " | 20 | — | — | H |
| 7 | tridecyl-O— | 10 | — | — | H |
| 8 | " | 11 | — | — | H |
| 9 | " | 12 | — | — | H |
| 10 | " | 13 | — | — | H |
| 11 | " | 14 | — | — | H |
| 12 | " | 15 | — | — | H |
| 13 | " | 16 | — | — | H |
| 14 | " | 17 | — | — | H |
| 15 | " | 18 | — | — | H |
| 16 | " | 19 | — | — | H |
| 17 | " | 20 | — | — | H |
| 18 | " | 25 | — | — | H |
| 19 | " | 30 | — | — | H |
| 20 | " | 15 | — | — | Me |
| 21 | " | 17 | — | — | Me |
| 22 | " | 15 | — | — | COCH₃ |
| 23 | " | 17 | — | — | COCH₃ |
| 24 | ($C_{12}$-alkyl)-O— | 10 | — | — | H |
| 25 | " | 11 | — | — | H |

TABLE 1-continued

| Ex. No. | R⁴ | x | y | z | R⁵ |
|---|---|---|---|---|---|
| 26 | " | 12 | — | — | H |
| 27 | " | 13 | — | — | H |
| 28 | " | 14 | — | — | H |
| 29 | " | 15 | — | — | H |
| 30 | " | 16 | — | — | H |
| 31 | (C₁₂-alkyl)-O— | 17 | — | — | H |
| 32 | " | 20 | — | — | H |
| 33 | " | 15 | — | — | Me |
| 34 | " | 15 | — | — | COCH₃ |
| 35 | (C₁₄-alkyl)-O— | 10 | — | — | H |
| 36 | " | 11 | — | — | H |
| 37 | " | 12 | — | — | H |
| 38 | " | 13 | — | — | H |
| 39 | " | 14 | — | — | H |
| 40 | " | 15 | — | — | H |
| 41 | " | 16 | — | — | H |
| 42 | " | 17 | — | — | H |
| 43 | " | 18 | — | — | H |
| 44 | " | 19 | — | — | H |
| 45 | " | 20 | — | — | H |
| 46 | " | 25 | — | — | H |
| 47 | " | 30 | — | — | H |
| 48 | " | 40 | — | — | H |
| 49 | (C₁₆-alkyl)-O— | 10 | — | — | H |
| 50 | " | 15 | — | — | H |
| 51 | " | 20 | — | — | H |
| 52 | " | 40 | — | — | H |
| 53 | (C₁₈-alkyl)-O— | 15 | — | — | H |
| 54 | " | 20 | — | — | H |
| 55 | (C₉-alkyl)-CO—O— | 10 | — | — | Me |
| 56 | " | 11 | — | — | Me |
| 57 | " | 12 | — | — | Me |
| 58 | " | 13 | — | — | Me |
| 59 | " | 14 | — | — | Me |
| 60 | " | 15 | — | — | Me |
| 61 | " | 16 | — | — | Me |
| 62 | " | 20 | — | — | Me |
| 63 | (C₁₀-alkyl)-CO—O— | 10 | — | — | Me |
| 64 | (C₁₀-alkyl)-CO—O— | 15 | — | — | Me |
| 65 | " | 20 | — | — | Me |
| 66 | (C₁₁-alkyl)-CO—O— | 10 | — | — | Me |
| 67 | " | 11 | — | — | Me |
| 68 | " | 12 | — | — | Me |
| 69 | " | 13 | — | — | Me |
| 70 | " | 14 | — | — | Me |
| 71 | " | 15 | — | — | Me |
| 72 | " | 16 | — | — | Me |
| 73 | " | 17 | — | — | Me |
| 74 | " | 20 | — | — | Me |
| 75 | " | 25 | — | — | Me |
| 76 | (C₁₂-alkyl)-CO—O— | 10 | — | — | Me |
| 77 | " | 15 | — | — | Me |
| 78 | " | 20 | — | — | Me |
| 79 | " | 25 | — | — | Me |
| 80 | (C₁₃-alkyl)-CO—O— | 15 | — | — | Me |
| 81 | " | 10 | — | — | Me |
| 82 | " | 20 | — | — | Me |
| 83 | (C₁₅-alkyl)-CO—O— | 15 | — | — | Me |
| 84 | " | 20 | — | — | Me |
| 85 | (C₉-alkyl)-CO—O— | 10 | — | — | (C₉-alkyl)-CO |
| 86 | " | 15 | — | — | " |
| 87 | " | 20 | — | — | " |
| 88 | (C₁₁-alkyl)-CO—O— | 10 | — | — | (C₁₁-alkyl)-CO |
| 89 | " | 15 | — | — | " |
| 90 | " | 20 | — | — | " |
| 91 | " | 30 | — | — | " |
| 92 | (C₁₂-alkyl)-CO—O— | 10 | — | — | (C₁₂-alkyl)-CO |
| 93 | " | 15 | — | — | " |
| 94 | " | 20 | — | — | " |
| 95 | (C₁₃-alkyl)-CO—O— | 10 | — | — | (C₁₃-alkyl)-CO |
| 96 | " | 20 | — | — | " |
| 97 | (C₁₅-alkyl)-CO—O— | 10 | — | — | (C₁₅-alkyl)-CO |
| 98 | " | 15 | — | — | " |
| 99 | isotridecyl-O— | — | 5 | 10 | H |
| 100 | " | — | 2 | 10 | H |
| 101 | " | 10 | 2 | — | H |
| 102 | " | 10 | 5 | 10 | H |
| 103 (Genamin ® 0 200 Clariant) | C₁₈H₃₅/C₁₆H₃₁—N— \| (EO)₁₀H | 10 | — | — | H |
| 104 (Afilan ® PTU, Clariant) | C₁₅H₂₉/C₁₇H₃₃—CO—O— | 9 | 2 | — | Me |
| 105 (Genapol ® 3938, Clariant) | C₁₂H₂₅/C₁₄H₂₉—O— | 6 | 4 | — | H |

The sulfonylureas of the formula (I) can form salts in which the hydrogen of the —SO₂—NH— group is replaced by an agriculturally suitable cation. Examples of these salts are metal salts, in particular alkali metal salts (for example sodium or potassium salts) or alkaline earth metal salts, or else ammonium salts or salts with organic amines. Salt formation can also take place by addition of a strong acid to the heterocycle moiety of the compounds of the formula (I). Acids which are suitable for this purpose are, for example, HCl, HNO₃, trichloroacetic acid, acetic acid or palmitic acid. Especially advantageous compounds are those in which the salt of the herbicide of the formula (I) is formed by replacing the hydrogen of the —SO₂—NH— group by a cation selected, for example, from the group consisting of the alkali metals, alkaline earth metals and ammonium ions, preferably sodium or tetrabutylammonium.

If the sulfonylureas of the formula (I) and/or their salts contain one or more asymmetric carbon atoms or else double bonds which are not specifically mentioned in the formula, these are still encompassed by the formula (I). The stereoisomers which are possible and which are defined by their specific spatial shape, such as enantiomers, diastereoisomers, Z- and E- isomers, are all encompassed by the formula (I) and can be obtained by customary methods from mixtures of the stereoisomers or else prepared by stereoselective reactions in combination with the use of stereochemically pure starting materials. The abovementioned stereoisomers in pure form and also their mixtures can thus be employed in accordance with the invention.

Sulfonylureas of the formula (I) and their salts are known in principle (see, for example, EP-A-342 569, EP-A-574 418, EP-A-723 534 and EP-A-757 679, which are expressly incorporated herein by way of reference); however, the fact that they are outstandingly suitable for use as combination partners in mixtures with surfactants B) is not evident from the prior art.

Preference is given to sulfonylureas of the formula (I) and/or salts thereof in which a) $R^1$ is CO—($C_1$–$C_4$-alkoxy) and $R^2$ is halogen, preferably iodine, or $R^2$ is $CH_2$—$NHR^e$, where $R^e$ is an acyl radical, preferably $C_1$–$C_4$-alkylsulfonyl, or b) $R^1$ is CO—N—($C_1$–$C_4$-alkyl)₂ and $R^2$ is $NHR^e$, where $R^e$ is an acyl radical, preferably formyl, or c) $R^1$ is $C_2$–$C_4$-alkoxy and $R^2$ is H.

Preference is also given to sulfonylureas of the general formula (I) and/or salts thereof in which the radical $R^2$ is in the position para to the radical $R^1$.

Examples of compounds of the formula (I) and/or their salts which may be mentioned are:

A1=N-(4,6-dimethoxypyrimid in-2-ylaminocarbonyl)-2-methoxycarbonyl-5-acetylaminobenzenesulfonamide A2=N-(4,6-dimethoxypyrimidin-2-ylaminocarbonyl)-2-methoxycarbonyl-5-(N-formyl-N-methylaminomethyl)benzenesulfonamide sodium salt A3=N-(4,6-dimethoxypyrimidin-2-ylaminocarbonyl)-2-methoxycarbonyl-5-acetylamino)benzenesulfonamide sodium salt A4=N-(4,6-dimethoxypyrimidin-2-ylaminocarbonyl)-2-methoxycarbonyl-5-(N-methyl-N-propionylamino)benzenesulfonamide sodium salt A5=N-(4,6-dimethoxypyrimidin-2-ylaminocarbonyl)-2-methoxycarbonyl-5-(N-isopropionylmethylamino)benzenesulfonamide sodium salt A6=N-(4,6-dimethoxypyrimidin-2-ylaminocarbonyl)-2-methoxycarbonyl-5-(N-methoxycarbonylaminomethyl)benzenesulfonamide sodium salt A7=N-(4,6-dimethoxypyrimidin-2-ylaminocarbonyl)-2-(N ,N-dimethylaminocarbonyl)-5-(N-methoxycarbonylamino)benzene-sulfonamide sodium salt A8=N-(4,6-dimethoxypyrimidin-2-ylaminocarbonyl)-2-(N,N-dimethylaminocarbonyl)-5-(N-formylamino)benzenesulfonamide (foramsulfuron)

A9=N-(4,6-dimethoxypyrimidin-2-ylaminocarbonyl)-2-(N,N-dimethylaminocarbonyl)-5-(N-propionylamino)benzenesulfonamide sodium salt A10=N-(4,6-dimethoxypyrimidin-2-ylaminocarbonyl)-2-methoxycarbonyl-5-(N-methylsulfonylaminomethyl)benzenesulfonamide sodium salt (mesosulfuronmethyl-sodium)

A11=N-(4,6-dimethoxypyrimidin-2-ylaminocarbonyl)-2-methoxycarbonyl-5-(N-methylsulfonylaminomethyl)benzenesulfonamide (mesosulfuron-methyl)

A12=N-(4,6-dimethoxypyrimidin-2-ylaminocarbonyl)-2-methoxycarbonyl-5-(N-methoxycarbonylaminomethyl)benzenesulfonamide sodium salt A13=N-(4-methoxy-6-methyl-1,3,5-triazin-2-ylaminocarbonyl)-2-methoxycarbonyl-5-iodobenzenesulfonamide (iodosulfuron-methyl)

A14=N-(4-methoxy-6-methyl-1,3,5-triazin-2-ylaminocarbonyl)-2-methoxycarbonyl-5-iodobenzenesulfonamide sodium salt (iodo-sulfuron-methyl-sodium)

A15=N-(4,6-dimethoxypyrimidin-2-ylaminocarbonyl)-2-methoxycarbonyl-5-(N-methylsulfonyl-N-methylaminomethyl)benzenesulfonamide A16=N-(4,6-dimethoxypyrimidin-2-ylaminocarbonyl)-2-ethoxybenzene-sulfonamide (ethoxysulfuron)

A17=N-(4,6-dimethoxypyrimidin-2-ylaminocarbonyl)-2-ethoxybenzene-sulfonamide sodium salt (ethoxysulfuron-sodium)

A18=N-(4,6-dimethoxypyrimidin-2-ylaminocarbonyl)-2-(N,N-dimethylaminocarbonyl)-5-(N-formylamino)benzenesulfonamide sodium salt (foramsulfuron-sodium)

As component A), it is also possible to use mixtures of two or more sulfonylureas of the formula (I) and/or their salts. Examples of such mixtures are mixtures of two or more of the compounds A1 to A15 mentioned above, such as A8+A13, A8+A14, A10+A13, A10+A14, A11+A13 or A11+A14.

An acyl radical for the purpose of the present description means the radical of an organic acid which is formed formally by eliminating an OH group from the organic acid, for example the radical of a carboxylic acid and radicals of acids derived therefrom, such as thiocarboxylic acid, optionally N-substituted iminocarboxylic acids or the radicals of carbonic monoesters, optionally N-substituted carbamic acids, sulfonic acids, sulfinic acids, phosphonic acids, phosphinic acids.

An acyl radical is preferably formyl or acyl selected from the group consisting of CO—$R^z$, CS—$R^z$, CO—$OR^z$, CS—$OR^z$, CS—$SR^z$, $SOR^z$ and $SO_2R^z$, where $R^z$ is in each case a $C_1$–$C_{10}$-hydrocarbon radical such as $C_1$–$C_{10}$-alkyl or $C_6$–$C_{10}$-aryl which is unsubstituted or substituted, for example by one or more substituents selected from the group consisting of halogen, such as F, Cl, Br, I, alkoxy, haloalkoxy, hydroxyl, amino, nitro, cyano or alkylthio, or $R^z$ is aminocarbonyl or aminosulfonyl, the two last-mentioned radicals being unsubstituted, N-monosubstituted or N,N-disubstituted, for example by substituents selected from the group consisting of alkyl and aryl.

Acyl is, for example, formyl, haloalkylcarbonyl, alkylcarbonyl such as ($C_1$–$C_4$)-alkylcarbonyl, phenylcarbonyl, it being possible for the phenyl ring to be substituted, or is alkyloxycarbonyl, such as ($C_1$–$C_4$)-alkyloxycarbonyl, phenyloxycarbonyl, benzyloxycarbonyl, alkylsulfonyl, such as ($C_1$–$C_4$)-alkylsulfonyl, alkylsulfinyl, such as ($C_1$–$C_4$)-alkylsulfinyl, N-alkyl-1-amino-alkyl, such as N—($C_1$–$C_4$)-alkyl-1-amino-($C_1$–$C_4$)-alkyl and other radicals of organic acids.

Carbon-containing radicals are organic radicals which contain at least one carbon atom, preferably 1 to 40 carbon atoms, particularly preferably 1 to 30 carbon atoms, very particularly preferably 1 to 20 carbon atoms, and furthermore at least one atom of one or more other elements of the Periodic Table of the Elements, such as H, Si, N, P, O, S, F, Cl, Br or I. Examples of carbon-containing radicals are unsubstituted or substituted hydrocarbon radicals which may be attached directly or via a heteroatom such as Si, N, S, P or O to the skeleton, unsubstituted or substituted heterocyclyl radicals which may be attached directly or via a heteroatom such as Si, N, S, P or O to the skeleton, carbon-containing acyl radicals or cyano.

The term heteroatom is to be understood as meaning elements of the Periodic Table of the Elements different from carbon and hydrogen, for example Si, N, S, P, O, F, Cl, Br or I.

Hydrocarbon(oxy) radicals are straight-chain, branched or cyclic and saturated or unsaturated aliphatic or aromatic hydrocarbon(oxy) radicals, for example alkyl, alkenyl, alkynyl, -cycloalkyl, cycloalkenyl or aryl and the hydrocarbonoxy radicals which correspond to these hydrocarbon radicals, such as alkoxy, alkenyloxy, alkynyloxy, cycloalkoxy, cycloalkenyloxy or aryloxy; aryl is a mono-, bi- or polycyclic aromatic system, for example phenyl, naphthyl, tetrahydronaphthyl, indenyl, indanyl, pantalenyl, fluorenyl and the like, preferably phenyl; a hydrocarbon radical is preferably alkyl, alkenyl or alkynyl having 1 to 30 carbon atoms or cycloalkyl having 3, 4, 5, 6 or 7 ring atoms or phenyl.

Substituted radicals, such as substituted hydrocarbon (oxy) radicals, for example substituted alkyl, alkenyl, alkynyl, cycloalkyl, cycloalkenyl or aryl, and the hydrocarbonoxy radicals which correspond to these hydrocarbon radicals, such as alkoxy, alkenyloxy, alkynyloxy, cycloalkoxy, cycloalkenyloxy or aryloxy, or substituted heterocyclyl radicals, denote, for example, a substituted radical derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the saturated hydrocarbon-containing radicals mentioned, such as alkenyl, alkynyl, alkenyloxy, alkynyloxy, etc. In the case of radicals having carbon atoms, preference is given to those having 1 to 4 carbon atoms, in particular 1 or 2 carbon atoms. Preference is generally given to substituents selected from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy and chlorine. Cycloalkyl is a carbocyclic saturated ring system, preferably with 3–6 carbon atoms, for example cyclopropyl, cyclobutyl, cyclopentyl or cyclohexyl.

The carbon-containing radicals such as alkyl, alkoxy, haloalkyl, haloalkoxy, alkylamino and alkylthio and the corresponding unsaturated and/or substituted radicals can in each case be straight-chain or branched in the carbon skeleton. Unless otherwise specified, in the case of these radicals, the lower carbon skeletons, for example those having 1 to 6 carbon atoms and, in the case of unsaturated groups, having 2 to 6 carbon atoms are preferred. Alkyl radicals, also in the composite meanings such as alkoxy, haloalkyl and the like, are, for example, methyl, ethyl, n- or isopropyl, n-, iso-, t- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meanings of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

A heterocyclic radical or ring (heterocyclyl radical) can be saturated, unsaturated or heteroaromatic and unsubstituted or substituted; it preferably contains one or more heteroatoms in the ring, preferably selected from the group consisting of N, O and S; it is preferably an aliphatic heterocyclyl radical having 3 to 7 ring atoms or a heteroaromatic radical having 5 or 6 ring atoms and contains 1, 2 or 3 heteroatoms. The heterocyclic radical can, for example, be a heteroaromatic radical or ring (heteroaryl), such as, for example, a mono-, bi- or polycyclic aromatic system in which at least one ring contains one or more heteroatoms, for example pyridyl, pyrimidinyl, pyridazinyl, pyrazinyl, triazinyl, thienyl, thiazolyl, oxazolyl, furyl, pyrrolyl, pyrazolyl and imidazolyl, or it is a partially or fully hydrogenated radical such as oxiranyl, oxetanyl, pyrrolidyl, piperidyl, piperazinyl, dioxolanyl, morpholinyl, tetrahydrofuryl. Suitable substituents for a substituted heterocyclic radical are the abovementioned substituents and additionally also oxo. The oxo group can also be present on the hetero ring atoms which may exist in different oxidation states, for example in the case of N and S.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine, and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly for haloalkenyl and other halogen-substituted radicals.

The herbicidal compositions according to the invention comprising compounds of the formula (I) and/or their salts and surfactants B) have excellent herbicidal activity and, in a preferred embodiment, superadditive effects. Owing to the improved control of harmful plants by the herbicidal compositions according to the invention, it is possible to reduce the application rate and/or to increase the safety margin. Both make sense, from an economical and an ecological point of view. The amounts of A)+B) to be employed and the ratio of the components A):B) depend on a whole range of factors.

In a preferred embodiment, the herbicidal compositions according to the invention are characterized in that they have a synergistically effective amount of a combination of the compounds of the formula (I) and/or their salts with surfactants B). Here, it has to be emphasized in particular that even in combinations where the application rates or weight ratios of A):B) are such that a synergism cannot be demonstrated clearly in each case—for example owing to the fact that the individual compounds are usually employed in the combination in very different application rates or else because the control of harmful plants by the individual compounds is already very good—a synergistic action is generally inherent to the herbicidal compositions of the invention.

Components A) and B) of the herbicidal compositions according to the invention can be formulated separately or applied by the tank mix method, or they can be contained together in a ready-to-use formulation which can then be applied in a customary manner, for example in the form of a spray liquor.

The herbicidal compositions according to the invention can be formulated in various ways depending on the prevailing biological and/or physico-chemical parameters. Examples of suitable formulation options are: wettable powders (WP), water-soluble powders (SP), water-soluble concentrates (SL), emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th Edition 1986, Wade van Valkenburg, "Pesticide Formulations", Marcel Dekker, N.Y., 1973; K. Martens, "Spray Drying" Handbook, 3rd Ed. 1979, G. Goodwin Ltd., London.

The necessary formulation auxiliaries, such as inert materials, surfactants, solvents and other additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte"[Surface-active ethylene oxide adducts], Wiss. Verlagsgesell., Stuttgart 1976; Winnacker-Küchler, "Chemische Technologie", Volume 7, C. Hauser Verlag Munich, 4th Edition 1986.

Based on these formulations it is also possible to produce combinations with other agrochemically active compounds which differ from component A), such as insecticides, acaricides, herbicides, fungicides, safeners, fertilizers such as ammonium sulfate, ammonium hydrogen sulfate, urea or mixtures thereof, and/or growth regulators, for example in the form of a ready-to-use formulation or as tank mix.

Wettable powders are preparations which are uniformly dispersible in water and which contain, in addition to the active compound A) and/or the surfactant B), and in addition to a diluent or inert substance, also surfactants of ionic and/or nonionic nature which are different from surfactant B) (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzene-sulfonates, sodium lignosulfonate, sodium 2,2'-dinaphthylmethane-6,6'-disulfonate, sodium dibutylnaphthalenesulfonate or else sodium oleoylmethyltaurinate. To prepare the wettable powders, the herbicidally active compounds A) and/or surfactants B) are finely ground, for example in customary apparatus such as hammer mills, fan mills and air-jet mills, and are mixed simultaneously or subsequently with the formulation auxiliaries.

Emulsifiable concentrates are prepared by dissolving the active compound A) and/or the surfactant B) in an organic solvent, for example 3-methoxypropanol, mono-, di- or oligoesters such as dimethyl malonate, dimethyl succinate, dimethyl glutarate or dimethyl adipate, butanol, cyclohexanone, dimethylformamide, xylene or else relatively high-boiling aromatic compounds, oils (such as soya oil methyl ester or rapeseed oil methyl ester) or hydrocarbons or mixtures of the organic solvents with addition of one or more surfactants of ionic and/or nonionic nature differing from surfactant B) (emulsifiers). Suitable for use as emulsifiers are, for example: calcium alkylarylsulfonates, such as calcium dodecylbenzene-sulfonate, or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters, or polyoxyethylene sorbitan esters, for example polyoxyethylene sorbitan fatty acid esters (for example Atplus® 309F from Uniquema) or else block copolymers, for example based on ethylene oxide and propylene oxide.

Water-soluble concentrates are obtained, for example, by dissolving the active compound A) and/or the surfactant B) in water or a water-miscible solvent and adding, if appropriate, further auxiliaries such as water-soluble surfactants.

Dusts are obtained by grinding the active compound A) and/or the surfactant B) with finely divided solid substances, for example talc, natural clays, such as kaolin, bentonite and pyrophyllite, or diatomaceous earth.

Suspension concentrates can be water- or oil-based. They can be prepared, for example, by wet milling using commercially customary bead mills, with or without the addition of surfactants different from surfactant B), as already mentioned above, for example, in the case of the other formulation types.

Emulsions, for example oil-in-water emulsions (EW), can be prepared, for example, by means of stirrers, colloid mills and/or static mixers using aqueous organic solvents and, if appropriate, surfactants different from surfactant B), as already mentioned above, for example, in the case of the other formulation types.

Granules can be prepared either by spraying the active compound A) and/or surfactant B) onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds A) and/or surfactants B) can also be granulated in the manner which is customary for the preparation of fertilizer granules—if desired as a mixture with fertilizers.

Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see, for example, processes in "Spray-Drying Handbook", 3rd Ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, N.Y. 1973, pp. 8–57.

For further details on the formulation of crop protection products, see, for example, G. C. Klingman, "Weed Control as a Science", John Wiley and Sons, Inc., N.Y., 1961, pages 81–96 and J. D. Freyer, S. A. Evans, "Weed Control Handbook", 5th Ed., Blackwell Scientific Publications, Oxford, 1968, pages 101–103.

The herbicidal compositions according to the invention generally comprise from 0.01 to 99% by weight, in particular from 0.1 to 95% by weight, of one or more sulfonylureas of the formula (I) and/or their salts.

In wettable powders, the concentration of active compound is, for example, from about 10 to 90% by weight, the remainder to 100% by weight consisting of customary formulation constituents and, if appropriate, surfactants B). In emulsifiable concentrates, the concentration of active compound can be from about 1 to 90, preferably from 5 to 80, % by weight. Formulations in the form of dusts comprise from 1 to 30% by weight of active compound, preferably most commonly from 5 to 20% by weight of active compound, while sprayable solutions comprise from about 0.05 to 80, preferably from 2 to 50, % by weight of active compound. In the case of water-dispersible granules, the content of active compound depends partly on whether the active compound is in liquid or solid form and on the granulation auxiliaries, fillers, etc., that are used. In water-dispersible granules the content of active compound is, for example, between 1 and 95% by weight, preferably between 10 and 80% by weight.

In addition, said formulations of active compound may comprise the auxiliaries such as tackifiers, wetting agents, dispersants, emulsifiers, penetrants, preservatives, antifreeze agents, solvents, fillers, carriers, colorants, antifoams, adjuvants such as mineral or vegetable oils and derivatives thereof, evaporation inhibitors and pH and viscosity regulators which are customary in each case.

The herbicidal compositions according to the invention can be prepared by customary processes, for example by mixing the components with the aid of stirrers, shakers or (static) mixers.

In a preferred embodiment of this invention, the formulations comprising sulfonylureas of the formula (I) and/or their salts are mixed in the spray tank with surfactants B) and/or formulations thereof. To this end, the sulfonylureas of the formula (I) and/or their salts can be formulated, for example on the basis of kaolin, as water-dispersible granules, where the content of sulfonylureas of the formula (I) and/or their salts may vary within wide limits between 0.01 and 99% by weight, preferably between 0.5 and 80% by weight. In addition to the sulfonylureas of the formula (I) and/or their salts, these formulations may comprise further agrochemically active compounds, such as safeners, for example in an amount of from 0.1 to 50% by weight, preferably from 0.5 to 40% by weight. The surfactants B) can be added as pure substances or in formulated form, preferably as a liquid product, such as a water-soluble concentrate or an emulsifiable concentrate.

Ready-to-use formulations can be obtained by preparing, for example, emulsifiable concentrates or oil dispersions of sulfonylureas of the formula (I) and/or their salts, surfactants B)-and further auxiliaries. In the ready-to-use formulations, the amount of sulfonylureas of the formula (I) and/or their salts can vary within wide limits and is generally between 0.01 and 99% by weight, preferably between 0.1 and 60% by weight. The amount of surfactants B) can also vary within wide limits and is generally between 1 and 80% by weight, as a rule between 5 and 50% by weight. Finally, the ready-to-use formulations may also comprise further agrochemically active compounds such as safeners, for example in an amount of from 0.01 to 60% by weight, preferably from 0.1 to 40% by weight.

If appropriate, the formulations may comprise auxiliaries such as solvents, for example aromatic solvents, such as xylenes or mixtures of aromatic compounds from the Solvesso® series such as Solvesso® 100, Solvesso® 150 or Solvesso® 200 from Exxon; aliphatic or isoparaffinic solvents, such as products from the Exxol®-D or Isopur® series from Exxon; oils of vegetable or animal origin and derivatives thereof, such as rapeseed oils or rapeseed oil methyl esters; esters, such as butyl acetate; ethers, such as diethyl ether, THF or dioxane. The solvent content is preferably 1–95% by weight, particularly preferably 5–80% by weight. Further suitable auxiliaries are, for example, emulsifiers (preferred content: 0.1–10% by weight), dispersants (preferred content: 0.1–10% by weight) and thickeners (preferred content: 0.1–5% by weight), and, if appropriate, stabilizers, such as antifoams, water scavengers, acid scavengers and crystallization inhibitors.

The herbicidal compositions according to the invention can be used pre- or post-emergence, for example by spraying. The use of the mixtures allows the amount of preparation required for controlling weeds to be reduced considerably.

The surfactants B) to be used according to the invention are generally applied together with the sulfonylurea(s) A) or immediately afterward, preferably in the form of a spray liquor which comprises effective amounts of surfactants B) and sulfonylureas A) and, if appropriate, further customary auxiliaries. The spray liquor is preferably prepared based on water and/or an oil, for example a high-boiling hydrocarbon such as kerosene or paraffin. Here, the herbicidal compositions according to the invention can be realized as a tank mix or via a "ready-to-use formulation".

The weight ratio of sulfonylurea A) to surfactant B) can vary within a wide range and depends, for example, on the efficacy of the sulfonylurea. It is generally in a range of from 10:1 to 1:5000, preferably from 4:1 to 1:2000.

The application rates of the compound(s) of the formula (I) and/or their salts are generally between 0.1 and 200 g of AS/ha (AS=active substance, i.e. application rate based on the active compound), preferably between 0.5 and 100 g of ai/ha. The application rates of surfactants B) are generally between 1 and 5000 g of surfactant/ha; preference is given to from 10 to 2000 g of surfactant/ha.

The concentration of the surfactants B) to be used according to the invention in a spray liquor is generally from 0.05 to 4% by weight, preferably 0.1 to 1% by weight, in particular from 0.1 to 0.3% by weight, of surfactant.

The herbicidal compositions according to the invention have excellent herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the herbicidal compositions according to the invention, without these being a restriction to certain species.

Examples of weed species on which the active compounds act efficiently are, from amongst the monocotyledons, Avena, Lolium, Alopecurus, Phalaris, Echinochloa, Digitaria, Setaria and also Cyperus species mainly from the annual sector and, from amongst the perennial species, Agropyron, Cynodon, Imperata and Sorghum, and also perennial Cyperus species.

In the case of the dicotyledonous weed species, the spectrum of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The compositions according to the invention also effect outstanding control of harmful plants which occur under the specific conditions of rice-growing such as, for example, Echinochloa, Sagittaria, Alisma, Eleocharis, Scirpus and Cyperus.

If the herbicidal compositions according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the herbicidal compositions according to the invention are applied post-emergence to the green parts of the plants, growth also stops drastically a very short time after the treatment and the weed plants remain at the developmental stage of the point in time of application, or they die completely after a certain time, so that in this manner competition from the weeds, which is harmful to the crop plants, is eliminated at a very early point in time and in a sustained manner.

Although the herbicidal compositions according to the invention have an excellent herbicidal activity against monocotyledonous and dicotyledonous weeds, crop plants of economically important crops, for example dicotyledonous crops such as soya, cotton, oilseed rape, sugar beet, in particular soya, or gramineous crops such as wheat, barley, rye, rice or corn, are not damaged at all, or only to a negligible extent. For these reasons, the present compounds are highly suitable for selectively controlling undesired plant growth in plantings of agriculturally useful plants including ornamental plants.

In addition, the herbicidal compositions according to the invention have outstanding growth-regulating properties in crop plants. They engage in the plant metabolism in a regulating manner and can thus be employed for the targeted control of plant constituents and for facilitating harvesting, such as for example by provoking desiccation and stunted growth. Furthermore, they are also suitable for generally regulating and inhibiting undesirable vegetative growth, without destroying the plants in the process. Inhibition of vegetative growth plays an important role in many monocotyledonous and dicotyledonous crops because lodging can be reduced hereby, or prevented completely.

Owing to their herbicidal and plant-growth-regulatory properties, the herbicidal compositions according to the invention can also be employed for controlling harmful plants in crops of known or still to be developed genetically engineered plants. The transgenic plants generally have particularly advantageous properties, for example resistance to certain pesticides, in-particular certain herbicides, resistance to plant diseases or causative organisms of plant diseases, such as certain insects or microorganisms such as fungi, bacteria or viruses.

Other particular properties relate, for example, to the quantity, quality, storage stability, composition and to specific ingredients of the harvested product. Thus, transgenic plants having an increased starch content or a modified quality of the starch or those having a different fatty acid composition of the harvested product are known.

The use of the compositions according to the invention in economically important transgenic crops of useful and ornamental plants, for example of cereals, such as wheat, barley, rye, oats, millet, rice, manioc and corn, or else in crops of sugar beet, cotton, soya, oilseed rape, potato, tomato, pea and other vegetable species is preferred. The compositions according to the invention can preferably be used as herbicides in crops of useful plants which are resistant or which have been made resistant by genetic engineering toward the phytotoxic effects of the herbicides.

When using the herbicidal compositions according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crop is resistant, and an effect on the growth and the yield of the transgenic crop plants.

The invention therefore also provides for the use of the compositions according to the invention as herbicides for controlling harmful plants, preferably in crop plants, where the crop plants may also be transgenic crop plants.

The herbicidal compositions according to the invention can also be used in a non-selective manner for controlling undesirable vegetation, for example on paths, open spaces, industrial sites or rail tracks.

Owing to the relatively low application rate of the herbicidal compositions according to the invention, they are, as a rule, already well tolerated. In particular, the combinations according to the invention lead to a reduction in the absolute application rate in comparison with the individual application of a herbicidal active compound.

If, if desired, the tolerance and/or selectivity of the herbicidal compositions according to the invention are to be increased further, it may be advantageous to apply them jointly as a mixture or staggered in time one after the other together with safeners or antidotes.

Compounds which are suitable as safeners or antidotes for the herbicidal compositions according to the invention are disclosed, for example, in EP-A-333 131 (ZA-89/1960), EP-A-269 806 (U.S. Pat. No. 4,891,057), EP-A-346 620 (AU-A-89/34951) and the international patent applications PCT/EP 90/01966 (WO-91108202) and PCT/EP 90102020 (WO-911078474) and the literature cited therein or can be prepared by the processes described therein. Other suitable safeners are known from EP-A-94 349 (U.S. Pat. No. 4,902,304), EP-A-191 736 (U.S. Pat. No. 4,881,966) and EP-A-0 492 366 and the literature cited therein.

In a preferred embodiment, the herbicidal compositions of the present invention therefore additionally comprise C) of one or more compounds which act as safeners or antidotes.

Preferred antidotes or safeners or groups of compounds which are suitable as safeners or antidotes in the herbicidal compositions of the invention are, inter alia:

a) Compounds of the dichlorophenylpyrazoline-3-carboxylic acid type, preferably compounds such as ethyl 1-(2,4-dichlorophenyl)-5-(ethoxycarbonyl)-5-methyl-2-pyrazoline-3-carboxylate (compound C1-1, mefenpyr-diethyl) and related compounds as they are described in the international application WO 91/07874 (PCT/EP 90102020);

b) Dichlorophenylpyrazolecarboxylic acid derivatives, preferably compounds such as ethyl 1-(2,4-dichlorophenyl)-5-methylpyrazole-3-carboxylate (compound C1-2), ethyl 1-(2,4-dichlorophenyl)-5-isopropylpyrazole-3-carboxylate (compound C1-3), ethyl 1-(2,4-dichlorophenyl)-5-(1,1-dimethylethyl) pyrazole-3-carboxylate (compound C1-4), ethyl 1-(2, 4-dichlorophenyl)-5-phenylpyrazole-3-carboxylate (compound C1-5) and related compounds as are described in EP-A-0 333 131 and EP-A-0 269 806;

c) Compounds of the triazolecarboxylic acid type, preferably compounds such as ethyl 1-(2,4-dichlorophenyl)-5-trichloromethyl-(1H)-1,2,4-triazole-3-carboxylate (compound C1-6, fenchlorazole-ethyl) and related compounds (see EP-A-0 174 562 and EP-A-0 346 620);

d) Compounds of the dichlorobenzyl-2-isoxazoline-3-carboxylic acid type, compounds of the 5-benzyl- or 5-phenyl-2-isoxazoline-3-carboxylic acid type, preferably compounds such as ethyl 5-(2,4-dichlorobenzyl)-2-isoxazoline-3-carboxylate (compound C1-7) or ethyl 5-phenyl-2-isoxazoline-3-carboxylate (compound C1-8) and related compounds as they are described in the international patent application WO 91/08202 (PCT/EP 90/01966);

e) Compounds of the 8-quinolinoxyacetic acid type, preferably compounds such as 1-methylhex-1-yl 5-chloro-8-quinolinoxyacetate (cloquintocet-mexyl, C2-1), 1,3-dimethylbut-1-yl 5-chloro-8-quinolin-oxyacetate (C2-2), 4-allyloxybutyl 5-chloro-8-quinolinoxyacetate (C2-3), 1-allyloxyprop-2-yl 5-chloro-8-quinolinoxyacetate (C2-4), ethyl 5-chloro-8-quinolinoxyacetate (C2-5), methyl 5-chloro-8-quinolinoxyacetate (C2-6), allyl 5-chloro-8-quinolinoxyacetate (C2-7), 2-(2-propylidene-iminooxy)-1-ethyl 5-chloro-8-quinolinoxy-acetate (C2-8), 2-oxoprop-1-yl 5-chloro-8-quinolinoxyacetate (C2-9) and related compounds as they are described in EP-A-0 086 750, EP-A-0 094 349 and EP-A-0 191 736 or EP-A-0 492 366;

f) Compounds of the 5-chloro-8-quinolinoxymalonic acid type, preferably compounds such as diethyl 5-chloro-8-quinolinoxy-malonate, diallyl 5-chloro-8-quinolinoxymalonate, methyl ethyl 5-chloro-8-quinolinoxymalonate and related compounds as they have been described and proposed in the German patent application EP-A-0 582 198;

g) Active compounds of the type of the phenoxyacetic- or -propionic acid derivatives or of the aromatic carboxylic acids, such as, for example, 2,4-dichlorophenoxyacetic acid (and its esters) (2,4-D), 4-chloro-2-methylphenoxypropionic ester (mecoprop), MCPA or 3,6-dichloro-2-methoxybenzoic acid (and its esters) (dicamba);

h) Compounds of the 5,5-diphenyl-2-isoxazoline-3-carboxylic acid type, preferably ethyl 5,5-diphenyl-2-isoxazoline-3-carboxylate (C3-1, isoxadifen-ethyl);

i) Compounds known as safeners, for example for rice, such as fenclorim (=4,6-dichloro-2-phenylpyrimidine, Pesticide Manual, 11th Edition, 1997, pp. 511–512), dimepiperate (=S-(1-methyl-1-phenylethyl) 1-piperidinecarbothioate, Pesticide Manual, 11th Edition, 1997, pp. 404–405), daimuron (=1-(1-methyl-1-phenylethyl)-3-p-tolylurea, Pesticide Manual, 11th Edition, 1997, p. 330), cumyluron (=3-(2-chlorophenylmethyl)-1-(1-methyl-1-phenyl-ethyl) urea, JP-A-601087254), methoxyphenone (=3,3'-dimethyl-4-methoxybenzophenone), CSB (=1-bromo-4-(chloromethyl-sulfonyl)benzene, CAS Reg. No. 54091-06-4).

In addition, at least some of the compounds mentioned are described in EP-A-0 640 587, which is herewith referred to for publication purposes.

j) A further important group of compounds which are suitable as safeners and antidotes is disclosed in WO 95107897.

The safeners (antidotes) of the above groups a) to j) reduce or contain phytotoxic effects which may occur in crops of useful plants when employing the herbicidal compositions according to the invention without adversely affecting the efficacy of the herbicides against harmful plants. This allows the field of application of the herbicidal compositions according to the invention to be widened considerably, and, in particular, the use of safeners allows combinations to be employed whose use has previously only been possible with limitations or with insufficient success, i.e. combinations which, without safeners, had a poor spectrum of action and led to insufficient control of harmful plants when applied at low dosage rates.

The herbicidal compositions according to the invention and the abovementioned safeners can be applied together (as a ready-to-use formulation or by the tank mix method) or in succession in an arbitrary sequence. The weight ratio of safener:herbicide (compound(s) of the formula (I) and/or the salts thereof) may vary within wide limits and is preferably in the range of 1:100 to 100:1, in particular 1:10 to 10:1. The amounts of herbicide(s) and safener(s) which are optimal in each case depend usually on the type of the herbicidal composition and/or on the safener used and on the nature of the plant stand to be treated.

Depending on their properties, the safeners of type C) may be used for pretreating the seed of the crop plant (seed dressing) or incorporated into the seed furrow prior to sowing or applied together with the herbicide mix before or after emergence of the plants.

The pre-emergence treatment includes not only the treatment of the area under cultivation before sowing, but also the treatment of the areas under cultivation where seed has been sown but the plants have not yet emerged. The joint application together with the herbicide mix is preferred. To this end, tank mixes or ready-to-use formulations may be employed.

The required application rates of the safeners may vary within wide limits, depending on the indication and the herbicide used, and are, as a rule, in the range of 0.001 to 1 kg, preferably 0.005 to 0.2 kg, of active compound per hectare.

The present invention also relates to a method of controlling undesired plants, preferably in crop plants, which comprises applying a herbicidally active amount of the herbicidal composition according to the invention, for example to the plants, the parts of the plants, the seeds of the plants or the area under cultivation.

In a preferred variant of the method the herbicidal compositions according to the invention are applied in the form of tank mixes, the individual components, for example in the form of formulations, jointly being mixed in the tank with water or an oil liquor and the resulting spray mixture being applied. Since the crop plant tolerance of the combinations according to the invention is decidedly good while simultaneously effecting very good control of the harmful plants, the combinations can be considered as selective. In a preferred modification of the method, herbicidal compositions are therefore employed for the selective control of undesired plants.

The herbicidal compositions according to the invention can be applied in the customary manner, for example with water and/or oil as carrier in amounts of approximately 0.5–4000, preferably 100 to 1000, liters of spray liquor/ha. The compositions may also be applied by the low-volume and ultra-low-volume (ULV) methods and in the form of granules and microgranules.

A preferred application relates to the use of herbicidal compositions which comprise components A and B in a synergistically effective amount.

The invention also includes herbicidal compositions which comprise mixtures of one or more combination partners A), preferably A8, A10, A11, A13, A14, A16, A17 and/or A18 and one or more combination partners B), if appropriate in combination with one or more safeners C).

Preferred examples of the herbicidal compositions according to the invention which may be mentioned are the following combinations of A8, A10, A11, A13, A14, A16, A17 and/or A18 with surfactants B), without the combinations being limited to those mentioned explicitly:

A8 in combination with one of the surfactants of group B1 to B105 (see Table 1)

A10 in combination with one of the surfactants of group B1 to B105 (see Table 1)

A11 in combination with one of the surfactants of group B1 to B105 (see Table 1)

A13 in combination with one of the surfactants of group B1 to B105 (see Table 1)

A14 in combination with one of the surfactants of group B1 to B105 (see Table 1)

A16 in combination with one of the surfactants of group B1 to B105 (see Table 1)

A17 in combination with one of the surfactants of group B1 to B105 (see Table 1)

A18 in combination with one of the surfactants of group B1 to B105 (see Table 1)

A8+A13 in combination with one of the surfactants of group B1 to B105 (see Table 1)

A8+A14 in combination with one of the surfactants of group B1 to B105 (see Table 1)

A11+A13 in combination with one of the surfactants of group B1 to B105 (see Table 1)

A11+A14 in combination with one of the surfactants of group B1 to B105 (see Table 1)

In the combinations listed, it may be advantageous to use a safener, as this may reduce possible damage to the crop plant caused by sulfonylurea derivatives or other herbicidally active compounds.

In addition, the herbicidal compositions of the present invention may comprise, to round off the properties, additionally, in most cases in minor amounts, one, two or more agrochemically active compounds differing from component A) (for example herbicides, insecticides or fungicides).

Thus, there are numerous possibilities of combining a plurality of active compounds with one another and using them jointly for controlling harmful plants, preferably in crop plants, without deviating from the essence of the invention.

To summarize, it can be said that, when sulfonylureas of the formula (I) and/or their salts are used together with one or more surfactants B), an excellent herbicidal activity is obtained. The activity of the herbicidal compositions according to the invention in a preferred embodiment is more pronounced than the activity of the individual components employed when used on their own.

These effects permit, inter alia, a reduction of the application rate, the control of a broader spectrum of broad-leafed weeds and weed grasses, the closure of activity gaps, also with respect to resistant species, a more rapid and safer action, a longer duration of action, a complete control of the harmful plants with only one or a few applications, and a widening of the period of use. Moreover, the herbicidal compositions according to the invention have better selectivity in crop plants.

The abovementioned properties are needed in practical control of weeds to keep agricultural crops free of undesirable competing plants and thus to secure and/or increase the quality and quantity of the yields. With respect to the described properties, the prior art is considerably surpassed by these novel combinations. In addition, the combinations according to the invention permit, in an excellent manner, the control of harmful plants which are otherwise resistant.

EXAMPLES

Seeds or rhizome pieces of monocotyledonous and dicotyledonous weeds were placed in sandy loam soil in plastic pots, covered with soil and grown in a greenhouse under good growth conditions. Three weeks after seeding, the test plants were treated in the three-leaf stage. The herbicidal compositions, formulated as wettable powders or as emulsion concentrates, were sprayed onto the green parts of the plants at an application rate of 600–800 l of water/ha (converted). The test plants were allowed to stand in the greenhouse under optimum growth conditions for about 3 to 4 weeks, and the effect of the preparations was then rated visually in comparison to untreated controls. The results are compiled in Table 1 below. The herbicidal compositions according to the invention have excellent herbicidal activity against economically important harmful plants.

TABLE 1

| Active compound/surtactant | g of AS/ha | g of surfactant/ha | Damage in % to ECHCG |
|---|---|---|---|
| A8/Genapol ® X150 | 2.5 | 2000 | 94 |
| A8/Genapol ® X060 | 2.5 | 2000 | 0 |

Abbreviations:
g of AS/ha: Gram of active substance/hectare
ECHCG: *Echinochloa crus galli*
A8: foramsulfuron
Genapol ® X150: surfactant having 15 ethylene oxide units
Genapol ® X060: surfactant having 6 ethylene oxide units

We claim:
1. An herbicidal composition comprising:
A) one or more sulfonylureas of the formula (I) and/or their salts:

(I)

wherein:
$R^1$ is $C_2$–$C_4$-alkoxy or CO—$R^a$, where $R^a$ is OH, $C_1$–$C_6$-alkoxy or $NR^bR^c$, where $R^b$ and $R^c$ independently of one another are identical or different and are H or $C_1$–$C_6$-alkyl, $R^2$ is halogen or $(A)_n$—$NR^dR^e$, where n is zero or 1, A is a group $CR^fR^g$, where $R^f$ and $R^g$ independently of one another are identical or different and are H or $C_1$–$C_6$-alkyl, $R^d$ is H or $C_1$–$C_6$-alkyl and $R^e$ is H, $C_1$–$C_6$-alkyl or an acyl radical, where $R^d$ and $R^e$ may also from a heterocyclic ring, $R^3$ is H or $C_1$–$C_6$-alkyl, M is zero or I, X and Y independently of one another are identical or different and are $C_1$–$C_6$-alkyl, $C_1$–$C_6$-alkoxy or $C_1$–$C_6$-alkylthio, where each of the three radicals mentioned is unsubstituted or substituted by one or more radicals selected from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, Z is CH or N, and B) one or more surfactants comprising as a structural element at least 10 alkylene oxide units.

2. The herbicidal composition claimed in claim 1, comprising, as component B), one or more surfactants of the formula (II)

$$R^4\text{—}(EO)_x(PO)_y(EO)_z\text{—}R^5 \quad (II)$$

in which

EO is an ethylene oxide unit,

PG is a propylene oxide unit, x is an integer from 1 to 50, y is an integer from 0 to 50, z is an integer from 0 to 50, where the sum (x+y+z) is $\geq 10$ and $\leq 150$, and $R^4$ is OH, an unsubstituted or substituted $C_1$–$C_{40}$-hydrocarbonoxy radical, an O-acyl radical or $NR^IR^{II}$ or $[NR^IR^{II}R^{III}]\oplus X\ominus$, where $R^I$, $R^{II}$, $R^{III}$, are identical or different and are H or an unsubstituted or substituted $C_1$–$C_{30}$-hydrocarbon radical which may be attached via a group $(EO)_w$, where w is an integer from 1 to 50, $X\ominus$ being an anion, and $R^5$ is H, an unsubstituted or substituted $C_1$–$C_{40}$-hydrocarbon radical, an acyl radical or $NR^IR^{II}$ or $[NR^IR^{II}R^{III}]\oplus X\ominus$, where $R^I$, $R^{II}$, $R^{III}$, are identical or different and are H or an unsubstituted or substituted $C_1$–$C_{30}$-hydrocarbon radical which may be attached via a group $(EO)_w$, where w is an integer from 1 to 50, $X\ominus$, being an anion.

3. The herbicidal composition as claimed in claim 1, additionally comprising one or more further components selected from the group consisting of agrochemically active compounds of a different type, additives conventionally used in crop protection, and formulation auxiliaries.

4. A method of controlling harmful plants, wherein the herbicidal composition as defined in claim 1 is applied to the plants, the parts of the plants, the seeds of the plants or the area under cultivation pre-emergence, post-emergence or pre-and post-emergence.

5. The method as claimed in claim 4 for selectively controlling harmful plants in crop plants.

6. The herbicidal composition according to claim 1, wherein X and Y independently of one another are identical or different and are $C_1$–$C_4$-alkyl or $C_1$–$C_4$-alkoxy.

7. A process for the preparation of a herbicidal composition as defined in claim 1, wherein the compound(s) of the formula (I) and/or the salts thereof is or are mixed with one or more surfactants B).

8. The process as claimed in claim 7, wherein components A) and B) are mixed with water and/or an oil by a tank mix method.

9. The herbicidal composition according to claim 1, wherein said one or more sulfonylureas of the formula (I) and/or their salts is selected from the group consisting of:

N-(4,6-dimethoxypyrimidin-2-ylaminocarbonyl)-2-methoxycarbonyl-5-acetylaminobenzenesulfonamide, N-(4,6-dimethoxypyrimidin-2-ylaminocarbonyl)-2-methoxycarbonyl-5-(N-formyl-N-methylaminomethyl)benzenesulfonamide sodium salt, N-(4,6-dimethoxypyrimidin-2-ylaminocarbonyl)-2-methoxycarbonyl-5-acetylamino)benzenesulfonamide sodium salt, N-(4,6-dimethoxypyrimidin-2-ylaminocarbonyl)-2-methoxycarbonyl-5-(N-methyl-N-propionylamino)benzenesulfonamide sodium salt, N-(4,6-dimethoxypyrimidin-2-ylaminocarbonyl)-2-methoxycarbonyl-5-(N-isopropionylmethylamino)benzenesulfonamide sodium salt, N-(4,6-dimethoxypyrimidin-2-ylaminocarbonyl)-2-methoxycarbonyl-5-(N-methoxycarbonylaminomethyl)benzenesulfonamide sodium salt, N-(4,6-dimethoxypyrimidin-2-ylaminocarbonyl)-2-(N,N-dimethylaminocarbonyl)-5-(N-methoxycarbonylamino)benzene sulfonamide sodium salt, N-(4,6-dimethoxypyrimidin-2-ylaminocarbonyl)-2-(N,N-dimethylaminocarbonyl)-5-(N-formylamino)benzenesulfonamide (foramsulfuron), N-(4,6-dimethoxypyrimidin-2-ylaminocarbonyl)-2-(N,N-dimethylaminocarbonyl)-5-(N-propionylamino)benzenesulfonamide sodium salt, N-(4,6-dimethoxypyrimidin-2-ylaminocarbonyl)-2-methoxycarbonyl-5-(N-methylsulfonylaminomethyl)benzenesulfonamide sodium salt (mesosulfuron-methyl-sodium), N-(4,6-dimethoxypyrimidin-2-ylaminocarbonyl)-2-methoxycarbonyl-5-(N-methylsulfonylaminomethyl)benzenesulfonamide (mesosulfuron-methyl), N-(4,6-dimethoxypyrimidin-2-ylaminocarbonyl)-2-methoxycarbonyl-5-(N-methoxycarbonylaminomethyl)benzenesulfonamide sodium salt, N-(4-methoxy-6-methyl-1,3,5-triazin-2-ylaminocarbonyl)-2-methoxycarbonyl-5-iodobenzenesulfonamide (iodosulfuron-methyl), N-(4-methoxy-6-methyl-1,3,5-triazin-2-ylaminocarbonyl)-2-methoxycarbonyl-5-iodobenzenesulfonamide sodium salt (iodosulfuron-methyl-sodium), N-(4,6-dimethoxypyrimidin-2-ylaminocarbonyl)-2-methoxycarbonyl-5-(N-methylsulfonyl-N-methylaminomethyl)benzenesulfonamide, and N-(4,6-dimethoxypyrimidin-2-ylaminocarbonyl)-2-(N,N-dimethylaminocarbonyl)-5-(N-formylamino)benzenesulfonamide sodium salt (foramsulfuron-sodium).

10. The herbicidal composition according to claim 1, wherein:
$R^1$ is CO—($C_1$–$C_4$-alkoxy) and $R^2$ is halogen or $R^2$ is $CH_2$—$NHR^e$, wherein $R^e$ is an acyl radical.

11. The herbicidal composition according to claim 10, wherein said halogen is iodine.

12. The herbicidal composition according to claim 10, wherein said acyl radical is $C_1$–$C_4$ alkylsulfonyl.

13. The herbicidal composition according to claim 1, wherein $R^1$ is CO—N—($C_1$–$C_4$-alkyl)$_2$ and $R^2$ is $NHR^e$, wherein $R^e$ is an acyl radical.

14. The herbicidal composition according to claim 13, wherein said acyl radical is formyl.

* * * * *